United States Patent [19]

Sumner, Jr. et al.

[11] Patent Number: 5,424,457
[45] Date of Patent: Jun. 13, 1995

[54] PROCESS FOR THE PRODUCTION OF STEROL AND TOCOPHEROL CONCENTRATES

[75] Inventors: Charles E. Sumner, Jr.; Scott D. Barnicki; Martin D. Dolfi, all of Kingsport, Tenn.

[73] Assignee: Eastman Chemical Company, Kingsport, Tenn.

[21] Appl. No.: 250,221

[22] Filed: May 27, 1994

[51] Int. Cl.$^6$ .............................. C07J 75/00; C07J 9/00
[52] U.S. Cl. ............................. 549/408; 549/410; 549/413; 552/502; 552/545
[58] Field of Search ............... 552/545, 502; 549/408, 549/410, 413

[56] References Cited

U.S. PATENT DOCUMENTS

| | | | |
|---|---|---|---|
| 2,432,181 | 12/1947 | Trent | 167/81 |
| 2,729,655 | 1/1956 | Miller et al. | 260/397.25 |
| 3,153,055 | 10/1964 | Brown et al. | 260/345.6 |
| 3,335,154 | 8/1967 | Smith | 260/345.6 |
| 3,840,570 | 10/1974 | Julian | 260/397.25 |
| 4,148,810 | 4/1979 | Struve | 260/397.25 |
| 4,374,776 | 2/1983 | Struve | 260/397.25 |
| 4,451,564 | 5/1984 | Struve et al. | 435/55 |

Primary Examiner—Johann Richter
Assistant Examiner—Kimberly J. Kestler
Attorney, Agent, or Firm—Bernard J. Graves, Jr.; Harry J. Gwinnell

[57] ABSTRACT

A process is provided which allows the isolation of sterols and a tocopherol concentrate in high yields from a deodorizer distillate (DOD) mixture obtained from the processing of, for example, soybean oils. Treatment of DOD with methanol at preferably 200°–220° C. in the presence of a monoalkyl- or dialkyl-tin compound results in the conversion of fatty acids and fatty acid esters into fatty acid methyl esters (FAME) and the liberation of free sterols and glycerin without appreciable degradation of tocopherols or sterols. The process can also be carried out in two steps where glycerin is used in the initial step and the fatty acids are converted into glycerides allowing the water of reaction to be removed as it is formed. The FAME produced by both methods are removed by a stripping operation to give a concentrate that allows the isolation of sterols in high yield and high purity and the isolation of a tocopherol concentrate by molecular distillation.

36 Claims, No Drawings

PROCESS FOR THE PRODUCTION OF STEROL AND TOCOPHEROL CONCENTRATES

FIELD OF THE INVENTION

This invention belongs to the field of organic chemistry. In particular, this invention relates to a process for the manufacture of sterol and tocopherol concentrates from deodorizer distillate.

BACKGROUND OF THE INVENTION

Tocopherols and sterols are useful alcohol compounds that can be found in vegetable oils. Tocopherols are used as a raw material for vitamin E synthesis, and sterols can be used as raw materials for synthesis of medicines such as cortisone and various sexual hormones. Treatment of vegetable oils with steam and vacuum produces a byproduct referred to as deodorizer distillate, or deodorizer sludge. This deodorizer distillate is rich in tocopherols and sterols, but also contains a multitude of other compounds. A typical batch of deodorizer distillate may contain free fatty acids (39%), a mixture of mono, di- and tri-glycerides (30%), sterols and fatty acid esters of sterols (14% total), tocopherols (9%), and the remainder hydrocarbons.

Numerous methods have been proposed for the recovery of tocopherols and sterols from deodorizer distillates and related mixtures. For example, U.S. Pat. No. 2,432,181 teaches that tocopherols can be recovered from vegetable oils and fats by reacting the fatty acid glycerides with an aliphatic monohydric alcohol in the presence of an alkaline alcoholysis catalyst, followed by flash distillation of residual alcohol, glycerol and fatty acid esters.

U.S. Pat. No. 2,729,655 teaches that sterols can be recovered from distillate by saponification and acidulation to convert glycerides and sterol esters to free fatty acids and free alcohols (glycerol, sterols respectively). The free fatty acids are esterified with a monohydric lower alcohol. The sterols are crystallized by the addition of a hydrocarbon/water solvent to the mixture.

U.S. Pat. No. 3,153,055 teaches a process for the isolation of sterols and tocopherols from deodorizer distillate by esterification of higher fatty acids into lower monohydric alcohol esters under strongly acidic conditions. The sterols and tocopherols are fractionally extracted from the esterification product with a combination of polar and nonpolar solvents.

U.S. Pat. No. 3,335,154 teaches that the distillate is saponified and acidulated to convert glycerides and sterol esters to free fatty acids and free alcohols (glycerol, sterols respectively). The free fatty acids are esterified with a monohydric lower alcohol and mineral acid catalyst. The sterols are precipitated by the addition of water to the mixture, and the tocopherols are concentrated by removal of the fatty esters by molecular distillation.

U.S. Pat. No. 3,840,570 teaches that sterols can be concentrated from a plant-derived source by phase separation caused by the addition of a water-alcohol solvent. Sterol esters are saponified with an alkali metal base and free sterols are crystallized from an aprotic solvent.

U.S. Pat. No. 4,148,810 teaches that sterols can be isolated by transesterification of distillate with methanol, catalyzed by alkali metal alcoholates or alkali metal hydroxides. The sterols are isolated from the transesterification mixture by adduct formation with calcium chloride in an aprotic solvent.

U.S. Pat. Nos. 4,374,776 and 4,451,564 teach a method for the concentration of sterols by base-catalyzed transesterification of distillate residues with a lower monohydric alcohol, followed by molecular distillation. The base catalyst is an alkali metal alcoholate or alkali metal hydroxide. The use of alkaline transesterification catalysts in the methods discussed above suffer a major disadvantage in that they require that the mixture be free of all acidic components that would neutralize the alkaline catalyst. This is most unsatisfactory in the case of tocopherols in that they are phenolic compounds and can react with methoxide ion. Other drawbacks of the above processes are that they require multiple reactor systems and processing steps, product purification, relatively low yields, and low through-put.

SUMMARY OF THE INVENTION

The object of this invention is to provide an efficient, economical process for the isolation of tocopherols and sterols from the deodorizer distillate of vegetable oil processing. In this invention, the deodorizer distillate is subjected to an esterification/transesterification step utilizing a lower alcohol and an alkyltin catalyst, crystallization to remove sterols, followed by distillation to remove lower alcohol and the fatty acid lower alcohol esters, and finally a molecular distillation to concentrate the tocopherols. Alternatively, the lower alcohols and/or fatty acid lower alcohol esters may be removed prior to crystallization. As a further aspect of this invention, there is provided alkyltin catalyzed esterification/transesterification of free fatty acids and fatty acid esters in the presence of tocopherols in which approximately 55 to 90% of the sterol esters are converted.

DETAILED DESCRIPTION OF THE INVENTION

The present invention provides a process for the esterification/trans-esterification of a deodorizer distillate mixture, said mixture comprised of sterols, tocopherols, free fatty acids, mono, di-, and tri-glycerides, which comprises reacting said mixture with a $C_1$–$C_8$ alcohol in the presence of a monoalkyl- or dialkyltin, or phenyl phosphonic acid catalyst, at a temperature of about 150°–240° C., to form fatty acid esters, glycerin, and free sterols.

We have found that mono- and dialkyltin compounds and phenyl phosphonic acid catalyze the transesterification of fatty acid esters, such as sterol esters, with, for example, methanol without significant degradation of the tocopherol compounds while at the same time providing a relatively high conversion. For example, treatment of the deodorizer distillate with methanol and dibutyltin oxide at 200° C. converts essentially all fatty acid esters to fatty acid methyl esters (FAME) and the corresponding free alcohols in a time span of less than 4 hours without any observed degradation of the sterols or tocopherols. It is believed that other lower alcohols can be substituted for methanol. The reaction is generally much faster at 220° C. Although other transition metals that are known to catalyze transesterification reactions are observed to catalyze the transesterification of deodorizer distillate, all are observed to degrade the tocopherols to some extent or are not as active as the alkyltin catalysts. In a typical reaction, 500 g of deodorizer distillate, 346 g of methanol, and 0.708 g of dibutyl tin oxide are heated at 200° C. for 4 hours. The reaction mixture is distilled first at atmospheric pressure to remove methanol, and the resulting residue is filtered. Water (22 g) is added to the filtrate, and the resulting mixture is allowed to cool to around 25° C. which results in crystallization of the sterols. The sterols are collected by filtration, and the mother liquor is distilled at reduced pressure to remove FAME and glycerol. The residue from the distillation is subjected to a molecular distillation step to isolate the tocopherols which come overhead in the distillation. The molecular distillation is carried out at pressures between about 50 to 1000 microns and temperatures of about 140° to 250° C. Any apparatus capable of achieving such conditions (e.g., centrifugal molecular still, falling film evaporator, or wiped film evaporator) is suitable for the molecular distillation step. The sludge from the molecular distillation is discarded. The process is described in more detail in the Experimental Section below.

Thus, as a further aspect of the present invention, there is provided a process for recovering sterols and tocopherols from a deodorizer distillate mixture, said mixture comprised of sterols, tocopherols, free fatty acids, mono, di-, and tri-glycerides, said process comprising the steps
a) reacting the deodorizer distillate mixture with a $C_1$–$C_8$ alcohol in the presence of a monoalkyl or dialkyltin or phenyl phosphonic acid catalyst at a temperature of about 150°–240° C.;
b) removing $C_1$–$C_8$ alcohols by distillation;
c) crystallization of sterols and isolation of said sterols; followed by
d) removing $C_1$–$C_8$ esters of fatty acids by distillation; and
e) molecular distillation of the resulting mixture to provide a concentrated tocopherol mixture.

As an alternative process there is provided a process for recovering sterols and tocopherols from a deodorizer distillate mixture, said mixture comprised of sterols, tocopherols, free fatty acids, mono, di-, and tri-glycerides, said process comprising the steps
a) reacting the deodorizer distillate mixture with a $C_1$–$C_8$ alcohol in the presence of a monoalkyl or dialkyltin or phenylphosphonic acid catalyst at a temperature of about 150°–240° C.;
b) removing $C_1$–$C_8$ esters of fatty acids and $C_1$–$C_8$ alcohols by distillation;
c) crystallization of sterols and isolation of said sterols;
d) molecular distillation of the resulting mixture to provide a concentrated tocopherol mixture.

In this process, preferred alkyl and dialkyltin catalysts include butyl stannoic acid, dibutyltin oxide, dibutyltin dilaurate, dibutyltin-bis(2-ethylhexanoate, butyltin-tris-(2-ethyl hexanoate), dioctyltin oxide, butyltin chloride dihydroxide, dibutyltin dimethoxide, dibutyltin diacetate, dibutyltin glycerin, and the reaction product of dibutyltin oxide and fatty acid methyl esters. In general, such mono- and di-alkyltin compounds will have alkyl portions which are $C_1$–$C_{20}$ hydrocarbyl groups, optionally possessing acyl, carbonyl, and keto groups in the chain. It should be recognized that many of these alkyl and dialkyltin compounds exist in a variety of structural forms, generally containing from about 2 to about 6 tin atoms per molecule. See for example, Alleston et al., *J.C.S.*, (1963), p. 5744.

Other forms of tin, such as stannous oxide, stannic oxide, stannous acetate, or stannic acetate were found to be much less active than the alkyltin derivatives due to the low solubility of these compounds. The alkyltin compounds were either soluble or reacted quickly to provide a soluble species. This observation is illustrated in Examples 11–14.

The operative temperature range for the esterification/transesterification is 150°–240° C. and the preferred range is 190°–220°. Pressure is not critical, so long as the $C_1$–$C_8$ alcohol is maintained as a liquid.

An alternative process to the one described above involves treating the DOD with glycerol (i.e., glycerolysis) in the initial step in order to convert all of the fatty acids to glycerides, followed by treatment with, for example, methanol (or another $C_1$–$C_8$ alcohol) in order to convert the glycerides to FAME and glycerol. The glycerolysis reaction can be carried out with or without a catalyst. This two-step process has the advantage of removing the water of reaction before the introduction of methanol and thus avoids the expense of drying the excess methanol before it is recycled. Another advantage is that the glycerol produced in the methanolysis step can be recovered by decantation instead of by distillation. The glycerol thus obtained can be reused without any purification scheme. Most of the catalyst is present in the glycerol layer at the end of the methanolysis step and can thus be recycled to the process along with the recovered glycerol.

Thus, as a further aspect of the present invention, there is provided a two-step process for the esterification/trans-esterification of a deodorizer distillate mixture which comprises reacting in a first step, said mixture with glycerin optionally in the presence of a catalyst, followed by reacting in a second step the product from said first step with a $C_1$–$C_8$ alcohol in the presence of a monoalkyl or dialkyltin or phenyl phosphonic acid catalyst, to form fatty acid esters, glycerin, and free sterols, wherein in said first step, the water of esterification is continuously removed, and wherein at least 5 g, preferably 7–15 g, of glycerin is present per 100 g of deodorizer distillate mixture.

As a further alternative in the processes described herein, glycerin is added to the esterification/transesterification reaction mixture in a concentration of at least about 2 weight percent based on the weight of deodorizer distillate mixture. As will be shown below, this added glycerin provides advantages in separating tin catalysts from the reaction products during workup.

Thus, as a further aspect of the present invention, there is provided a process for recovering sterols and tocopherols from a deodorizer distillate mixture, said mixture comprised of sterols, tocopherols, free fatty acids, mono, di-, and tri-glycerides, said process comprising the steps
a) reacting the deodorizer distillate mixture with a $C_1$–$C_8$ alcohol in the presence of a monoalkyl or dialkyltin or phenyl phosphonic acid catalyst in the presence of added glycerin, wherein said added glycerin is present in a concentration of at least about 2 weight percent based on the weight of deodorizer distillate mixture;
b) removing $C_1$–$C_8$ alcohols by distillation;
c) crystallization of sterols and isolation of said sterols;
d) removing $C_1$–$C_8$ esters of fatty acids by distillation followed by;
e) molecular distillation of the resulting mixture to provide a concentrated tocopherol mixture.

In the above process, examples of $C_1$–$C_8$ alcohol is include methanol, ethanol, propanol, isopropanol, n- butanol, n-pentanol, n-hexanol, and the like. Methanol is preferred.

The distillation step, where the $C_1$-$C_8$ alcohol is removed is essentially a flash distillation, preferably at a temperature of about 45° C. to 150° C., and at atmosphere. The distillation of the fatty acid $C_1$-$C_8$ alcohol esters is done preferably at a pressure of about Torr to about 0.5 Torr, and a temperature of about 150° C. to 215° C. As noted above, the $C_1$-$C_8$ alcohols and $C_1$-$C_8$ esters of fatty acids can be removed either before or after the crystallization step. If both are removed prior to crystallization, it may also be desirable add a non polar organic solvent such as heptane or hexane to the solution.

In a further aspect of the present invention, the crystallization of the sterol component is performed by adding water or a water/methanol mixture to the FAME solution. By way of example, methanol is stripped from the crude transesterification product and the resulting mixture filtered through filter aid. Any excess glycerin could be separated at this point by decantation; the glycerin separates as the bottom phase. Water (amounting to 2-4% of the mixture by weight), or a methanol/water solution is then added and the mixture allowed to cool to give the sterols. The mixtures were found to filter rapidly, and the filter cakes are washed with cold heptane to give a white product by removing residual mother liquor stuck to the crystals. In addition to its simplicity, this crystallization scheme provides a method of separating the sterols from the tin catalyst.

Thus, as a further aspect of the present invention, there is provided a method for crystallization of sterols in a solution comprising a deodorizer distillate mixture, and at least about 2 weight percent of glycerin based on the weight of the deodorizer distillate mixture, said mixture comprised of sterols, tocopherols, free fatty acids, mono, di-, and tri-glycerides, wherein said mixture has been esterified/transesterified with a $C_1$-$C_8$ alcohol, which comprises the steps:

(a) removing excess $C_1$-$C_8$ alcohol at a temperature of about 60° C. to about 200° C. and at a pressure of about 50 torr to about 1 atmosphere to provide a top layer comprised of crude sterols, tocopherols, $C_1$-$C_8$ esters of fatty acids and mono-, di-, and tri-glycerides and a bottom layer comprised of glycerin;

(b) separation of the top layer by decantation;

(c) treatment of the top layer with 2-4%, by weight, of water or a water/$C_1$-$C_3$ alcohol solution; followed by (d) cooling said top layer to a temperature of about 0° C. to about 30° C. and separating crystalline sterols formed therein.

The sterols referred to herein are mostly stigmasterol, campesterol, and sitosterol, but the identity and proportions of each will vary depending on the source of the deodorizer distillate.

As a further aspect of the invention, the mother liquor from step (d) is subjected to molecular distillation to provide a concentrated tocopherol selection.

EXPERIMENTAL SECTION

Example 1—Sn

A 500 mL autoclave was charged with deodorizer distillate (100 g), methanol (79 g), and butylstannoic acid (0.18 g). The mixture was heated for 3 h at 200° C. The mixture was cooled and analyzed by a combination of gas chromatography and liquid chromatography for FAME, tocopherols, sterols, sterol esters, glycerides and glycerol. The results are listed in Table 1 along with the results of the comparative Examples 3 through 7.

Example 2—Mn

The procedure of Example 1 was followed except that 0.25 g of manganese diacetate tetrahydrate was used in place of butylstannoic acid.

Example 3—Zn

The procedure of Example 1 was followed except that 0.22 g of zinc acetate dihydrate was used in place of butylstannoic acid.

Example 4—Ti

The procedure of Example 1 was followed except that 0.28 g of tetraisopropyl orthotitanate was used in place of butylstannoic acid.

Example 5—La

The procedure of Example 1 was followed except that 0.32 g of lanthanum triacetate hydrate was used in place of butylstannoic acid, and the temperature was 180° C.

Example 6—Sn

The procedure of Example 1 was followed except that 0.24 g of dibutyltin oxide was used in the place of butylstannoic acid.

Example 7—No catalyst

The procedure of Example 1 was followed except that no catalyst was used.

Examples 8-10—Effect of Temperature on the Tin Catalyzed Transesterification A 2 liter hastalloy autoclave was charged with 500 g DOD, 346 g methanol, and 1.9 g of butylstannoic acid. The mixture was agitated and heated to the desired temperature. The mixture was sampled at 15, 30, and 60 minute intervals during the course of the reaction in order to monitor the progress of the reaction. The results are shown in Table 2.

Examples 11-14—Comparative Examples Using Other Tin Salts as Catalysts

The procedure of Example 1 was followed except that 1 mmole of either SnO, $SnO_2$, $Sn(OAc)_2$, and $Sn(OAc)_4$ were used as the catalysts in place of butylstannoic acid. The results are summarized in Table 3.

Example 15—Two-step Process Esterification and Transesterification

To a 500 mL 3-neck flask with a drain on the bottom and equipped with a mechanical stirrer, $N_2$ purge, steam condenser, Claisen head, and a heated addition funnel was added 250 g of DOD and 1.78 g (2.8 mmole) of dibutyltin dilaurate. The mixture was heated to 220° C. and 22 g of glycerol heated to 220° C. was added through the addition funnel. The resulting mixture was vigorously stirred and heated at 220° C. for 60 minutes while a stream of $N_2$ was passed through the mixture until the acid number was less than 1 meq KOH/g. The mixture was allowed to cool to 40° and transferred to a glass container through the bottom drain.

A 500 mL autoclave was charged with 110 g of the glycerolysis mixture described above and methanol g). The resulting mixture was heated at 200° C. for 3 hours. The mixture was allowed to cool, and was analyzed for products as in Example 1. The results are given in Table 4.

Example 16—Non-catalyzed Glycerolysis

To a 1 liter, 3-neck flask with a drain on the bottom and equipped with a mechanical stirrer, $N_2$ purge, steam condenser was added 500 g of DOD and 45 g of glycerol. The resulting mixture was heated at 220° C. for 2 hour with a $N_2$ purge of at least 30 mL/min until the acid number of the mixture was less than 2 meq KOH/g. The product mixture was allowed to cool to 50° C. and was transferred to a 2 liter autoclave, followed by 346 g of methanol and 1.06 g (4.3 mmole) of dibutyltin oxide. The resulting mixture was heated at 200° C. for 4 hours. The mixture was sampled at 15, 60, 120, and 240 minutes. It was found that the reaction was essentially complete within 2 hours. The product mixture was allowed to cool, and was transferred to a distillation flask equipped with a 10 inch vigreux column. The methanol was distilled from the mixture until the temperature of the residue reached 150° C. The residue was allowed to cool to 60° and was filtered into a separatory funnel. The glycerol (bottom) layer was separated and weighed 20 g and was 0.4% tin. The top layer weighed 351 g and contained 54 ppm tin. The composition of the oil is given in Table 4.

Example 17

Crystallization of Sterols

The crude methanolysis product obtained from the treatment of 500 g of deodorizer distillate with 340 g methanol, 50 g of glycerin, and 1 g of dibutyltin oxide for 3 h at 200° C., was charged to a 2 L distilling flask equipped with a 10 inch vigreux column and distilling head, and a $N_2$ inlet consisting of a 10 inch, 18 gauge needle. The mixture was gradually heated to 150° C. with a steady flow of $N_2$ through the needle while the methanol and water distilled overhead. The distillate was collected and weighed. The residue was allowed to cool to below 100° and was filtered through celite (filter aid) in a steam-jacketed funnel. The hot filtrate was transferred to a separatory funnel and the layers were separated while the filtrate was still hot. The glycerin layer (bottom) was weighed and analyzed for tin. The top layer was weighed (450–500 g) and transferred to a 1 L 3-neck flask equipped with a mechanical stirrer, thermowell, and reflux condenser and $N_2$ atmosphere The mixture was heated to 70° C. .and a solution of methanol (60 g) and water (20 g) was added while the mixture was vigorously stirred. The ratio of filtrate:methanol:water was 24:3:1. The resulting mixture was allowed to cool to 25° C. over about a one hour period. The sterols crystallized from solution during this time, and were collected by filtration through a 600 mL coarse glass frit. Filtration times (determined as the time required for the mother liquor level to reach the top of the filter cake) averaged about 5 minutes. The filter cake was compressed with a small beaker to remove excess mother liquor. The resulting filter cake was about 1 inch thick, and was washed twice with 25 mL portions of cold (5°) heptane and slurried twice with 75 mL portions. The resulting product was white in color (off-white if no glycerin was used in the transesterification), and was dried in high vacuum for 1 hour. The sterols (product) were analyzed for tin, water, sterols, FAME, sterol esters, and tocopherols (initially obtained products were analyzed for glycerides). The products were usually found to be greater than 98% pure sterols. The mother liquors were analyzed for tin as well as other components mentioned above. The heptane washings were evaporated and weighed. The procedure was identical for examples where the methanol/water amounts were varied.

TABLE 1

| | Comparison of Catalysts (Moles of Product) | | | | | |
|---|---|---|---|---|---|---|
| Example No. | Catalyst | FAME | Tocopherols | Sterols | Sterol Esters | Glycerides | Glycerol |
| Initial Mixture | | 0.004 | 0.021 | 0.006 | 0.022 | 0.038 | 0.000 |
| 1 | Sn* | 0.219 | 0.019 | 0.024 | 0.005 | 0.007 | 0.038 |
| 2 | Mn | 0.211 | 0.016 | 0.024 | 0.005 | 0.000 | 0.046 |
| 3 | Zn | 0.218 | 0.015 | 0.022 | 0.008 | 0.006 | 0.039 |
| 4 | Ti | 0.215 | 0.020 | 0.016 | 0.012 | 0.007 | 0.038 |
| 5 | La | 0.232 | 0.020 | 0.019 | 0.013 | 0.003 | 0.035 |
| 6 | Sn** | 0.229 | 0.018 | 0.028 | 0.003 | 0.002 | 0.035 |
| 7 | No Catalyst | 0.233 | 0.019 | 0.016 | 0.012 | 0.005 | 0.036 |

Total glycerides calculated as moles triglycerides.
*butyl stannoic acid
**dibutyl tin oxide

TABLE 2

| Effect of Temperature on the Transesterification of DOD (Moles Product) 500 g Deodorizer Distillate, 346 g Methanol, 9 mmole Catalyst | | | | | | | | | |
|---|---|---|---|---|---|---|---|---|---|
| Example No. | Temp. °C. | Time (min) | Fatty Acids | FAME | Glycerides | Glycerol | Sterol Esters | Sterols | Tocopherols |
| 8 | 220 | 90 | 0.01 | 1.155 | 0.022 | 0.164 | 0.02 | 0.147 | 0.102 |
| 9 | 200 | 360 | 0.01 | 1.269 | 0.02 | 0.18 | 0.015 | 0.137 | 0.115 |
| 10 | 180 | 360 | 0.01 | 1.307 | 0.035 | 0.182 | 0.04 | 0.143 | 0.113 |

Total glycerides calculated as moles triglycerides.

TABLE 3

Comparison of Tin Salts for Use as Methanolysis Catalysts for DOD (Moles Product)
100 g DOD; 2.5 Mole MeOH; 1 Mmole Cat.; 200 Deg; 3 H

| Example No. | Catalyst | FAME | Tocopherols | Sterols | Sterol Ester | Glycerides | Glycerol |
|---|---|---|---|---|---|---|---|
| 11 | SnO | 0.216 | 0.021 | 0.015 | 0.014 | 0.005 | 0.032 |
| 12 | SnO2 | 0.218 | 0.020 | 0.014 | 0.015 | 0.006 | 0.035 |
| 13 | Sn(OAc)2 | 0.165 | 0.021 | 0.012 | 0.017 | 0.011 | 0.013 |
| 14 | Sn(OAc)4 | 0.157 | 0.020 | 0.012 | 0.016 | 0.012 | 0.009 |

Total glycerides calculated as moles triglycerides.

TABLE 4

Two Step Esterification and Transesterification of DOD (Moles Product)

| Example No. | FAME | Tot TOC | Tot Sterol | Glycerides | Sterol Esters | Glycerol |
|---|---|---|---|---|---|---|
| 15 | 0.239 | 0.022 | 0.031 | 0.000 | 0.010 | 0.133 |
| 16 | 0.752 | 0.069 | 0.093 | 0.018 | 0.013 | 0.000 |

Total glycerides calculated as moles triglycerides.

The conditions of the methanolysis reaction are believed to be the most significant factor determining the quality of the sterols produced by this process. Table 5 lists the concentration of tin in the sterols as a function of the methanolysis reaction conditions.

TABLE 5

Effect of Reaction Conditions on Tin Content of Sterols Dibutyltin Oxide Catalyst

| Reaction No. | time (h) | Temp. (C.) | [catalyst] mmol | glycerin (g) | [Sn] ppm | Yield* |
|---|---|---|---|---|---|---|
| A | 2 | 200 | 2.8 | 0 | 525 | 0.092 |
| B | 4 | 200 | 1.4 | 0 | 60 | 0.158 |
| C | 4 | 200 | 5.7 | 0 | 60 | 0.152 |
| D | 2 | 220 | 8.4 | 0 | 3100 | 0.086 |
| E | 4 | 220 | 2.8 | 0 | 1650 | 0.091 |
| F | 3 | 220 | 2.8 | 0 | 1380 | 0.091 |
| G | 1.5 | 220 | 2.8 | 0 | 1400 | 0.098 |
| H | 2 | 220 | 2.9 | 0 | 1430 | 0.092 |
| I | 2 | 220 | 2.9 | 0 | 1250 | 0.103 |
| J | 4 | 220 | 4.3 | 50 | 18 | 0.092 |
| K | 1.5 | 220 | 4.3 | 50 | 19 | 0.096 |
| L | 3 | 200 | 4.3 | 50 | 0 | 0.099 |
| M | 3 | 200 | 4.3 | 25 | 0 | 0.093 |
| N | 3 | 200 | 4.3 | 10 | 183 | 0.091 |

*Calculated as the ratio of crude sterols to mother liquor

Addition of glycerin to the methanolysis gave sterols that consistently had less than 20 ppm tin and very white color. Analogous procedures using methanolysis product containing no added glycerin gave sterols that were around 0.1% tin even though the mother liquors had tin concentrations of only around 600 ppm. (This was evidence that the tin catalyst was being occluded in the sterol crystals.) In addition to the higher tin levels, these analogous crystallization products had a beige color.

The temperature at which the methanolysis reaction was carried out also affected the amount of tin remaining in the sterols. Reactions carried out at 200° C. appeared to produce sterols containing less tin than reactions carried out at 220°. In fact, it was possible to isolate sterols having no detectable amount of tin by carrying out the methanolysis reaction at 200° in the presence of added glycerin. The tin residues were lower even in reactions having no added glycerin when the temperature was kept near 200°.

The conditions of the crystallization affected the tin residues in the sterols to a lesser degree. It was found in the later stages of this work that methanol need not be added to the crystallization mixture. Table 6 lists the effects of water and methanol concentrations on the tin residues.

TABLE 6

Effect of Crystallization Conditions on Yield and Tin Content

| Condition | Sterols (ppm) | Mother liquor (ppm) | Yield (%) |
|---|---|---|---|
| standard | 0.106% | 598 | 76 |
| no water or methanol | 0.236% | 622 | 41 |
| methanol/ no water | 0.136% | 124 | 41 |
| H2O/no* methanol | 110 | 730 | 75 |
| MeOH/theoretical H2O | 758 | 564 | 56 |
| theoretical H2O/ no MeOH | 344 | 668 | 64 |
| standard/ add glycerin | 354 | 626 | 85 |
| 1% water (glycerin run) | 23 | 82 | 60 |
| 2% water (glycerin run) | 27 | 268 | 68 |

Standard is 4% water
% Yield was determined from the ratio of isolated sterols minus water content to the theoretical amount of sterols measured in the filtered oil.
*Methanolysis reaction was carried out at 220° C., others at 200° C., all for 2h For methanolysis mixtures having no added glycerin, the presence of methanol had a detrimental effect. The Example with water and no methanol shows that addition of water without methanol lowered the amount of tin in the sterols by an order of magnitude compared to the control run (standard) where methanol and water were added. An analogous procedure (added water but no methanol) used to crystallize sterols from a methanolysis mixture with added glycerin gave sterols having higher than usual tin-residues for mixtures having added glycerin; and also produced sterols that took longer to filter. It should be pointed out that the amount of water added was only 67% of the amount normally used.

The optimum amount of water needed to reproducibly give sterol crystals of sufficient shape and size has not been determined. Some water is needed (probably one molar equivalent) as can be seen from the "no water no methanol" example in Table 6 and the water analysis in Table 7. In this case, most of the sterols are left in the mother liquor. It is believed that the sterols crystallize as a hydrate. Table 7 lists the water analysis for several batches of isolated sterols.

TABLE 7

Ratio of Water to Isolated Sterols

| Experiment | % Water | Weight (g) | Molar Ratio Water/Sterol |
|---|---|---|---|
| O | 9.4 | 11.0 | 2.4 |
| P | 0.8 | 8.9 | 0.2 |
| Q | 6.2 | 41.5 | 1.5 |
| R | 2.3 | 41.5 | 0.5 |
| S | 0.8 | 11.4 | 0.2 |
| T | 2.7 | 21.3 | 0.6 |
| U | 1.5 | 17.9 | 0.3 |
| V | 3.3 | 47.3 | 0.8 |
| W | 2.2 | 31.3 | 0.5 |
| X | 16.2 | 48.9 | 4.4 |
| Y | 1.6 | 41.9 | 0.4 |
| Z | 4.9 | 42.1 | 1.2 |
| AA | 1.6 | 39.6 | 0.4 |
| BB | 6.6 | 41.7 | 1.6 |
| CC | 4.6 | 36.2 | 1.1 |
| DD | 5.3 | 39.7 | 1.3 |
| EE | 4.3 | 41.5 | 1.0 |
| FF | 4.3 | 40.3 | 1.0 |
| GG | 3.5 | 37.9 | 0.8 |

Average mol. wt of sterols were calculated to be 411.

In these examples, the sterols were collected by filtration, washed several times with heptane, and dried in a hard vacuum for an hour without heating. As can be seen, most samples retained about a 1:1 molar ratio of water. However, addition of one molar amount of water (slightly greater than one molar equivalent; example P) was not sufficient to crystallize all of the sterols. It could be that there is a relationship between the time of cooling of the crystallization mixture and the amount of water required to achieve a maximum yield of sterols. Any cooling time/water relationship has not been investigated.

The yield of sterols obtained from this process is naturally dependent upon the concentration of sterols in the raw DOD. The solubility of sterols in the mother liquor at 25° C. was estimated to be around 2%. Thus, the more sterols that are present in the deodorizer oil, the greater the fraction that are recovered by this process.

We claim:

1. A process for the esterification/transesterification of a deodorizer distillate mixture, said mixture comprised of sterols, tocopherols, free fatty acids, and mono, di-, and tri-glycerides, which comprises reacting said mixture with a $C_1$-$C_8$ alcohol in the presence of a monoalkyl- or dialkyltin, or phenylphosphonic acid catalyst, at a temperature of about 150°-240° C., to form fatty acid esters, glycerin, and free sterols.

2. The process of claim 1, wherein the temperature ranges of from about 200° C. to 220° C.

3. The process of claim 1, wherein the concentration of catalyst ranges from 100 ppm to 3000 ppm.

4. The process of claim 1, wherein the concentration of catalyst is about 400 ppm to 1600 ppm.

5. The process of claim 1, wherein the catalyst is selected from the group consisting of butyl stannoic acid, dibutyltin oxide, dibutyltin dilaurate, dibutyltin-bis(2-ethylhexanoate, butyltin-tris-(2-ethyl hexanoate), dibutyltin dimethoxide, dibutyltin diacetate, dibutyltin glycerin, dioctyltin oxide, butyltin chloride dihydroxide, and the reaction product of dibutyltin oxide and fatty acid methyl esters.

6. The process of claim 1, wherein the catalyst is dibutyltin oxide or dibutyltin dilaurate.

7. The process of claim 1, wherein the catalyst is butylstannoic acid or butyltin tris(2-ethylhexanoate).

8. The process of claim 1, wherein the catalyst is phenylphosphonic acid.

9. The process of claim 1, wherein the catalyst is the reaction product of dibutyltin oxide and fatty acid methyl esters.

10. The process of claim 1, wherein the $C_1$-$C_8$ alcohol is methanol or n-butanol.

11. A two-step process for the esterification/transesterification of a deodorizer distillate mixture which comprises reacting in a first step, said mixture with glycerin, optionally in the presence of a catalyst, followed by reacting in a second step the product from said first step with a $C_1$-$C_8$ alcohol in the presence of a monoalkyl- or dialkyltin, or phenyl phosphonic acid catalyst, at a temperature of about 150°-240° C., to form fatty acid esters, glycerin, and free sterols, wherein in said first step, the water of esterification is continuously removed, and wherein at least 5 g of glycerin is present per 100 g of deodorizer distillate mixture.

12. The process of claim 11, wherein the catalyst in the first step is a mono- or dialkyltin compound or phenylphosphonic acid.

13. The process of claim 11, wherein the catalyst in the first step is butyl stannoic acid.

14. The process of claim 11, wherein the catalyst in the second step is butyl stannoic acid.

15. The process of claim 11, wherein the catalyst is the reaction product of dibutyltin oxide and glycerol.

16. The process of claim 11, wherein the $C_1$-$C_8$ alcohol is methanol or n-butanol.

17. The process of claim 11, wherein the catalyst is the reaction product of dibutyltin oxide and fatty acid methyl esters.

18. A process for recovering sterols and tocophereols from a deodorizer distillate mixture, said mixture comprised of sterols, tocopherols, free fatty acids, and mono, di-, and tri-glycerides, said process comprising the steps a) reacting the deodorizer distillate mixture with a $C_1$-$C_8$ alcohol in the presence of a monoalkyl or dialkyltin or phenyl phosphonic acid catalyst at a temperature of about 150°-240° C.;

b) removing $C_1$-$C_8$ alcohols by distillation;

c) crystallizing the sterols and isolating said sterols; followed by d) removing $C_1$-$C_8$ esters of fatty acids by distillation; and e) molecularly distilling the resulting mixture to provide a concentrated tocopherol mixture.

19. The process of claim 18, wherein the catalyst is the reaction product of dibutyltin oxide and glycerol.

20. The process of claim 18, wherein the $C_1$-$C_8$ alcohol is methanol or n-butanol.

21. A process for recovering sterols and tocophereols from a deodorizer distillate mixture, said mixture comprised of sterols, tocopherols, free fatty acids, and mono, di-, and tri-glycerides, said process comprising the steps a) reacting the deodorizer distillate mixture with a $C_1$-$C_8$ alcohol in the presence of a monoalkyl or dialkyltin or phenylphosphonic acid catalyst;

b) removing $C_1$-$C_8$ esters of fatty acids and $C_1$-$C_8$ alcohols by distillation;

c) crystallizing the sterols and isolating said sterols;

d) molecularly distilling the resulting mixture to provide a concentrated tocopherol mixture.

22. The process of claim 21, wherein the catalyst is the reaction product of dibutyltin oxide and glycerol.

23. The process of claim 21, wherein the $C_1$–$C_8$ alcohol is methanol or n-butanol.

24. A process for recovering sterols and tocopherols from a deodorizer distillate mixture, said mixture comprised of sterols, tocopherols, free fatty acids, and mono, di-, and tri-glycerides, said process comprising the steps
   a) reacting the deodorizer distillate mixture with a $C_1$–$C_8$ alcohol in the presence of a monoalkyl or dialkyltin or phenylphosphonic acid catalyst, at a temperature of about 150°–240° C., in the presence of added glycerin wherein said added glycerin is present in a concentration of at least about 2 weight percent based on the weight of deodorizer distillate mixture;
   b) removing $C_1$–$C_8$ alcohols by distillation;
   c) crystallizing the sterols and isolating said sterols;
   d) removing $C_1$–$C_8$ esters of fatty acids by distillation followed by;
   e) molecularly distilling the resulting mixture to provide a concentrated tocopherol mixture.

25. The process of claim 24, wherein the catalyst is selected from the group consisting of butyl stannoic acid, dibutyltin oxide, dibutyltin dilaurate, dibutyltin-bis(2-ethylhexanoate, butyltin-tris-(2-ethyl hexanoate), dibutyltin dimethoxide, dibutyltin diacetate, dibutyltin glycerin, and the reaction product of dibutyltin oxide and fatty acid methyl esters.

26. The process of claim 24, wherein the catalyst is butyl stannoic acid.

27. The process of claim 24, wherein the catalyst is the reaction product of dibutyltin oxide and glycerol.

28. The process of claim 24, wherein the catalyst is the reaction product of dibutyltin oxide and fatty acid methyl esters.

29. The process of claim 24, wherein the $C_1$–$C_8$ alcohol is methanol or n-butanol.

30. A process for crystallization of sterols in a solution comprising a deodorizer distillate mixture, and at least about 2 weight percent of glycerin based on the weight percent of the deodorizer distillate mixture, said mixture comprised of sterols, tocopherols, free fatty acids, and mono, di-, and tri-glycerides, wherein said mixture has been esterified/transesterified with a $C_1$–$C_8$ alcohol, which comprises the steps:
   (a) removing excess $C_1$–$C_8$ alcohol at a temperature of about 60° C. to about 200° C. and at a pressure of about 50 torr to about 1 atmosphere to provide a top layer comprised of crude sterols and a bottom layer comprised of glycerin;
   (b) separating the top layer by decantation;
   (c) treating the top layer with 2–4% by weight water or a water/$C_1$–$C_3$ alcohol solution; followed by
   (d) cooling said top layer to a temperature of about 0° C. to about 30° C. and separating crystalline sterols formed therein.

31. The process of claim 30, wherein the esterification/transesterification is carried out in the presence of a mono- or di-alkyltin or phenyl phosphonic acid catalyst.

32. The process of claim 30, wherein the $C_1$–$C_8$ alcohol is methanol or n-butanol.

33. The process of claim 30, wherein the $C_1$–$C_8$ alcohol is methanol.

34. The process of claim 30, wherein in step (c) a methanol/water solution is utilized.

35. The process of claim 31 wherein the catalyst is selected from the group consisting of butyl stannoic acid, dibutyltin oxide, dibutyltin dilaurate, dibutyltin-bis(2-ethylhexanoate, butyltin-tris-(2-ethyl hexanoate), dibutyltin dimethoxide, dibutyltin diacetate, dibutyltin glycerin, and the reaction product of dibutyltin oxide and fatty acid methyl esters.

36. The process of claim 30, further comprising the step:
   (e) molecularly distilling remaining top layer to provide a concentrated tocopherol solution.

* * * * *